United States Patent
Hugg et al.

(10) Patent No.: US 7,920,670 B2
(45) Date of Patent: Apr. 5, 2011

(54) KEYHOLE COMPUTED TOMOGRAPHY

(75) Inventors: James William Hugg, Glenville, NY (US); Ravindra Mohan Manjeshwar, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 51 days.

(21) Appl. No.: 12/412,160

(22) Filed: Mar. 26, 2009

(65) Prior Publication Data
US 2009/0225934 A1   Sep. 10, 2009

Related U.S. Application Data

(63) Continuation-in-part of application No. 11/731,612, filed on Mar. 30, 2007, now Pat. No. 7,680,240.

(51) Int. Cl.
A61B 6/00 (2006.01)
(52) U.S. Cl. ............................. 378/4; 378/8
(58) Field of Classification Search .................. 378/4, 8, 378/20
See application file for complete search history.

(56) References Cited

U.S. PATENT DOCUMENTS

| | | | |
|---|---|---|---|
| 4,689,670 A | 8/1987 | Okazaki | |
| 5,053,958 A | 10/1991 | Tam | |
| 5,504,334 A | 4/1996 | Jansen | |
| 5,625,190 A | 4/1997 | Crandall | |
| 5,689,116 A | 11/1997 | Heukensfeldt | |
| 6,445,761 B1 * | 9/2002 | Miyazaki et al. | 378/8 |
| 6,522,712 B1 | 2/2003 | Yavuz et al. | |
| 6,654,440 B1 | 11/2003 | Hsieh | |
| 6,768,782 B1 * | 7/2004 | Hsieh et al. | 378/8 |
| 6,850,587 B1 | 2/2005 | Karimi et al. | |
| 7,006,677 B2 | 2/2006 | Manjeshwar | |
| 7,038,212 B2 | 5/2006 | Wollenweber | |
| 7,057,178 B1 | 6/2006 | Manjeshwar | |
| 7,129,495 B2 | 10/2006 | Williams | |
| 7,129,496 B2 | 10/2006 | Stearns | |
| 7,173,248 B2 | 2/2007 | Ross | |
| 7,330,535 B2 | 2/2008 | Arenson et al. | |
| 2002/0154737 A1 * | 10/2002 | Klotz et al. | 378/98.12 |
| 2003/0081715 A1 | 5/2003 | Tam | |
| 2004/0066911 A1 * | 4/2004 | Hsieh et al. | 378/901 |
| 2004/0136490 A1 * | 7/2004 | Edic et al. | 378/4 |
| 2004/0202283 A1 * | 10/2004 | Okumura et al. | 378/145 |
| 2004/0225214 A1 | 11/2004 | Trotter | |
| 2005/0111622 A1 * | 5/2005 | Bruder et al. | 378/95 |
| 2006/0097175 A1 | 5/2006 | Ganin | |

(Continued)

OTHER PUBLICATIONS

Ogawa et al.; A Reconstruction Algorithm from Truncated Projections, IEEE Transactions on Medical Imaging, vol. MI-3, No. 1, Mar. 1984, pp. 34-40. Wagner; Reconstructions from Restricted Region Scan Data—New Means to Reduce the Patient Dose, IEEE Transactions on Nuclear Science, vol. NS-26, No. 2, Apr. 1979, pp. 2866-2869.

(Continued)

Primary Examiner — Edward J Glick
Assistant Examiner — Alexander H Taningco
(74) Attorney, Agent, or Firm — Scott J. Asmus (57) ABSTRACT

A method of acquiring and reconstructing a computed tomography (CT) image is provided. A first scan of the full field of view (FOV) is acquired. A second scan of a smaller target FOV is then acquired by using a collimator to narrow the X-ray beam width. The CT image is iteratively reconstructed by replacing a key-hole region of the full FOV projection data with the target FOV projection data. An exemplary embodiment comprises imaging a heart (target FOV) within a torso (full FOV) over multiple heart beat cycles. A computer readable medium is further provided, including a program configured to reconstruct a CT image using the key-hole method.

21 Claims, 8 Drawing Sheets

U.S. PATENT DOCUMENTS

2006/0138315 A1    6/2006   Williams
2006/0145082 A1    7/2006   Stearns
2006/0151705 A1    7/2006   Manjeshwar
2006/0261275 A1   11/2006   Stearns
2006/0262894 A1   11/2006   Bernhardt et al.
2007/0217570 A1*   9/2007   Grasruck et al. ................ 378/53
2008/0253635 A1*  10/2008   Spies et al. ................... 382/131

OTHER PUBLICATIONS

Nalcioglu et al.; Limited Field of View Reconstruction in Computerized Tomography, IEEE Transactions on Nuclear Science, vol. NS-26, No. 1, Feb. 1979, pp. 1-6.

De Man et al.; An Interative Algorithm for Time-Resolved Reconstruction of a CT Scan of a Beating Heart, CT Systems and Applications Laboratory, GE Global Research, pp. 1-4, 2005.

* cited by examiner

KEYHOLE COMPUTED TOMOGRAPHY

CROSS REFERENCE TO RELATED APPLICATIONS

This application is a continuation-in-part of U.S. patent application Ser. No. 11/731,612 entitled "ITERATIVE RECONSTRUCTION OF TOMOGRAPHIC IMAGE DATA METHOD AND SYSTEM", filed Mar. 30, 2007, which is herein incorporated by reference.

BACKGROUND

The invention relates generally to non-invasive imaging. More particularly, the invention relates to methods and systems for targeted iterative reconstruction for use in non-invasive imaging.

In the fields of medical imaging and security screening, non-invasive imaging techniques have gained importance due to benefits that include unobtrusiveness, ease, and speed. In medical and research contexts, these imaging systems are used to image organs or tissues beneath the surface of the skin. A number of non-invasive imaging modalities exist today. A particular modality may be selected based upon the organ or tissue to be imaged, upon the spatial and/or temporal resolution desired, or upon whether structural or functional characteristics are of interest. Certain of these non-invasive imaging modalities collect tomographic data that includes sets of line integrals from multiple directions. Examples of these imaging modalities include X-ray computed tomography (CT) imaging, positron emission tomography (PET) imaging, single photon emission computed tomography (SPECT) imaging, magnetic resonance imaging (MRI) using projection reconstruction, and X-ray tomosynthesis.

Certain applications of these imaging modalities require high-resolution images of a targeted field of view (FOV) that is less than the full scan FOV of the imaging system. For example, in cardiac imaging, a high-resolution image of a small sub-region of the patient's anatomy may be desired. However, in X-ray tomography, reconstruction of the measured projection data may rely on measured projection data from outside the targeted FOV. While reconstruction of this targeted FOV is generally straightforward for analytical reconstruction algorithms (such as filtered back projection), iterative reconstruction techniques typically consider the targeted FOV and the regions of the full scan FOV that surround the targeted FOV. This is because iterative reconstruction techniques attempt to match the estimated projection data (derived from forward projection of an estimated image) to the measured projection data. However, if the estimated projection data do not support the signal from outside the targeted FOV, the estimated projection data cannot correctly match the measured projection data.

In general, the signal from outside the targeted FOV should be accounted for in the image reconstruction. If the signal from outside the targeted FOV is not accounted for, the entire signal from outside the targeted FOV may be assigned to the periphery of the targeted FOV or may produce aliasing artifacts inside the targeted FOV. This approach may result in a visible artifact at the periphery of the reconstructed image and quantitatively inaccurate regions throughout the reconstructed image. In other cases, when a targeted FOV less than the scan FOV is requested, the full scan FOV may be reconstructed at high resolution. Subsequently, the image for desired targeted FOV may be extracted from this image for the full scan FOV. This approach, however, reconstructs an image for a full pixel grid (e.g., a full scan) even though only a partial pixel grid for the targeted FOV was requested. As the computational time and image storage requirements grow significantly based on the number of pixels in the reconstruction, this approach may be computationally expensive.

BRIEF DESCRIPTION

The present technique provides a novel method and system for determining the amount of a substance contained within a region. In accordance with one embodiment of the present technique, a method is provided to acquire a computed tomography image. The method includes acquiring full FOV (background) computed tomography projection data, acquiring target FOV computed tomography projection data, and reconstructing the computed tomography image based on the background a and the target region projection data.

In accordance with another embodiment of the present technique, a method is provided to acquire a computed tomography (CT) image. The method includes acquiring a scout image of a patient with a computed tomography scanner, determining a target position in the scout image, determining a target field of view, positioning the target field of view near to an axis of rotation of the CT scanner, performing a full scan, and performing a target scan, wherein the target scan comprises blocking X-ray beams that are not transmitted through the target field of view.

In accordance with yet another embodiment of the present technique, a method is provided to reconstruct a CT image. The method includes masking out data in a target (key-hole) region of a full-FOV sinogram that is based on full-FOV projection data, and iteratively reconstructing the CT image based on replacing the masked out keyhole data with target FOV projection data.

In accordance with yet another embodiment of the present technique, a computer readable medium is provided, including a program configured to reconstruct a CT image based on full scan data associated with a CT full scan and target scan data associated with a CT target scan. Reconstructing the CT image comprises replacing at least a portion of the full scan data associated with a target field of view with at least a portion of the target scan data associated with the target field of view.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The embodiments discussed below provide a technique for dynamic CT imaging. More specifically, certain embodiments include acquiring at least one full field of view (FOV) (background) image and a plurality of images of a targeted FOV that is contained with the region associated with the background image. To provide for improved processing performance, in certain embodiments, data in the region of the background image that corresponds to the targeted FOV is replaced with the data from each of the images in the targeted FOV. In some embodiments, one or more of the plurality of images including the targeted FOV are reconstructed based on the data in the targeted FOV and the surrounding data of the background image. Accordingly, in certain embodiments, only a single CT scan of a patient is made to acquire the background image and data for processing and additional CT scans are restricted to the targeted FOV, thereby reducing the dose of X-radiation to the patient while accurately acquiring multiple images of the targeted FOV. In some embodiments, such a technique is used for dynamic imaging of the targeted FOV. In some embodiments, the targeted FOV includes a patient's heart, such that images of the heart may be taken over a period of time (e.g., one or more heartbeats) and reconstructed to provide a four-dimensional image using a first background image for processing image data of the targeted FOV of the heart. Before a detailed discussion of the system and methods are described in accordance with various embodiments of the present technique, it may be beneficial to discuss embodiments of imaging systems that may incorporate the system and methods described herein.

Figure 1:
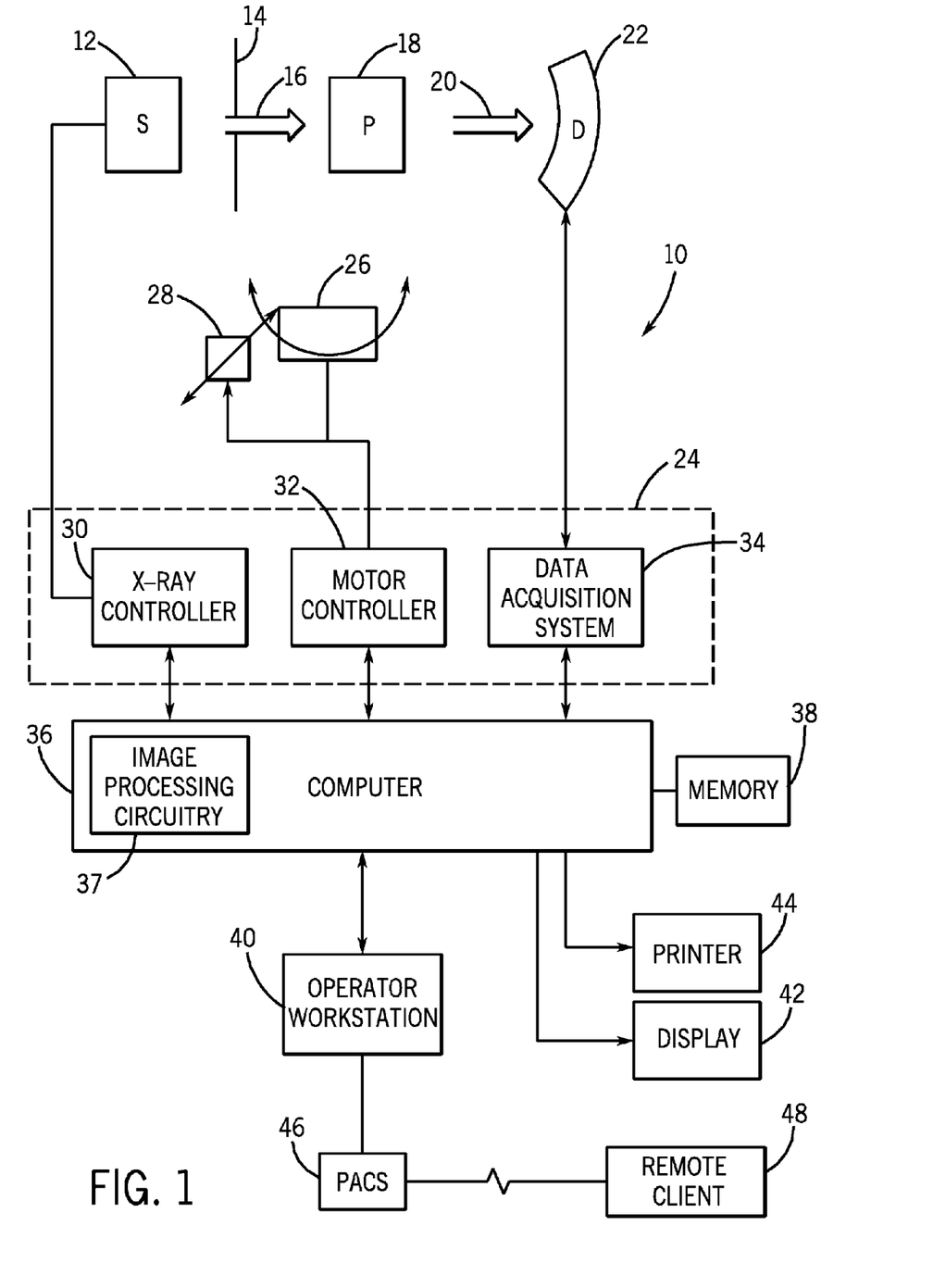
FIG. 1 is a diagrammatical illustration of an exemplary CT imaging system, in accordance with one aspect of the present technique.

Turning now to the figures, FIG. 1 is a diagram that illustrates an imaging system 10 for acquiring and processing image data. In the illustrated embodiment, system 10 is a CT system designed to acquire X-ray projection data, to reconstruct the projection data into a tomographic image, and to process the image data for display and analysis, in accordance with the present technique. Though the imaging system 10 is discussed in the context of medical imaging, the techniques and configurations discussed herein are applicable in other non-invasive imaging contexts, such as baggage or package screening or industrial nondestructive evaluation of manufactured parts. In the embodiment illustrated in FIG. 1, the CT imaging system 10 includes an X-ray source 12. As discussed in detail herein, the source 12 may include one or more conventional X-ray sources, such as an X-ray tube, or a distributed source configured to emit X-rays from different locations along a surface. For example, the source 12 may include one or more addressable solid-state emitters. Such solid-state emitters may be configured as arrays of field emitters, including one-dimensional arrays, i.e., lines, and two-dimensional arrays.

The source 12 may be positioned proximate to a collimator 14. The collimator 14 may consist of one or more collimating regions, such as lead or tungsten shutters, for each emission point of the source 12. The collimator 14 typically defines the size and shape of the one or more X-ray beams 16 that pass into a region in which a subject 18, such as a human patient is positioned. Each X-ray beam 16 may be generally fan-shaped or cone-shaped, depending on the configuration of the detector array and/or the desired method of data acquisition, as discussed below. An attenuated portion 20 of each X-ray beam 16 passes through the subject 18 and impacts a detector array, represented generally at reference numeral 22.

The detector 22 is generally formed by a plurality of detector elements that detect the X-ray beams 16 after they pass through or around the subject 18. Each detector element produces an electrical signal that represents the intensity of the X-ray beam 16 incident at the position of the detector element when the beam strikes the detector 22. Alternatively, each element of detector 22 may count incident photons in the X-ray beam 16 and may also determine their energy. Typically, the X-ray beam 16 is generated and the corresponding electrical signals are acquired at a variety of angular positions around the subject of interest so that a plurality of radiographic projection views can be collected. The electrical signals are acquired and processed to reconstruct an image that is indicative of the features within the subject 18, as discussed in further detail below.

A system controller 24 commands operation of the imaging system 10 to execute examination protocols and to process the acquired data. The source 12 is typically controlled by a system controller 24. Generally, the system controller 24 furnishes power, focal spot location, control signals and so forth, for the CT examination sequences. The detector 22 is coupled to the system controller 24, which commands acquisition of the signals generated by the detector 22. The system controller 24 may also execute various signal processing and filtration functions, such as initial adjustment of dynamic ranges, interleaving of digital image data, and so forth. In the present context, system controller 24 may also include signal-processing circuitry and associated memory circuitry. As discussed in greater detail below, the associated memory circuitry may store programs and routines executed by the system controller 24, configuration parameters, image data, and so forth. In one embodiment, the system controller 24 may be implemented as all or part of a processor-based system such as a general purpose or application-specific computer system.

In the illustrated embodiment of FIG. 1, the system controller 24 may control the movement of a linear positioning subsystem 28 and a rotational subsystem 26 via a motor controller 32. In an embodiment where the imaging system 10 includes rotation of the source 12 and/or the detector 22, the rotational subsystem 26 may rotate the source 12, the collimator 14, and/or the detector 22 about the subject 18. It should be noted that the rotational subsystem 26 might include a gantry (not shown) comprising both stationary components (stator) and rotating components (rotor). The linear positioning subsystem 28 may enable the subject 18, or more specifically a patient table that supports the subject 18, to be displaced linearly. Thus, the patient table may be linearly moved within the gantry or within an imaging volume (e.g., the volume located between the source 12 and the detector 22) and enable the acquisition of data from particular areas of the subject 18 and, thus the generation of images associated with those particular areas. Additionally, the linear positioning subsystem 28 may displace the one or more components of the collimator 14, so as to adjust the shape and/or direction of the X-ray beam 16. In embodiments comprising a stationary source 12 and a stationary detector 22, the rotational subsystem 26 may be absent. Similarly, in embodiments in which the source 12 and the detector 22 are configured to provide extended or sufficient coverage along the z-axis (i.e., the axis associated with the main length of the subject 18) and/or linear motion of the subject is not required, the linear positioning subsystem 28 may be absent.

As will be appreciated by those skilled in the art, the source 12 may be controlled by an X-ray controller 30 disposed within the system controller 24. The X-ray controller 30 may be configured to provide power and timing signals to the source 12. In addition, in some embodiments the X-ray controller 30 may be configured to selectively activate the source 12 such that tubes or emitters at different locations within the system 10 may be operated in synchrony with one another or independent of one another.

Further, the system controller 24 may comprise a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 may convert the sampled analog signals to digital signals prior to transmission to the data acquisition system 34.

In the depicted embodiment, a computer 36 is coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to produce representations of the line integrals of the attenuation coefficients of the subject 18 and the scanned objects. In one embodiment, the computer 36 contains image-processing circuitry 37 for processing and filtering the data collected from the detector 22. The processed data, commonly called projections, may then be filtered and backprojected by the image processing circuitry 37 to form an image of the subject 18 and/or the scanned area. As will be appreciated by those skilled in the art, the projections may be reconstructed into an image by using other well-known reconstruction algorithms, such as iterative reconstruction. The image processing circuitry 37 may apply geometry-dependent filtering to the processed data to improve image quality and enhance features or certain regions of interest. The identification and/or enhancement of features or regions of interest through such geometry-dependent filtering may be referred to as "computer-aided geometry determination." Once reconstructed, the image produced by the system 10 of FIG. 1 may reveal an internal region of interest of the subject 18 which can be used for diagnosis, evaluation, and so forth.

The computer 36 may comprise or communicate with a memory 38 that can store data processed by the computer 36, data to be processed by the computer 36, or routines to be executed by the computer 36, such as for processing image data in accordance with the present technique. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24 (i.e., scanning operations and data acquisition). Furthermore, the computer 36 may be configured to receive commands and scanning parameters from an operator via an operator workstation 40 which may be equipped with a keyboard and/or other input devices. An operator may, thereby, control the system 10 via the operator workstation 40. Thus, the operator may observe from the computer 36 the reconstructed image and other data relevant to the system 10, initiate imaging, select and apply image filters, and so forth. Further, the operator may manually identify features and regions of interest from the reconstructed image, or the operator may review features and regions of interest automatically identified and/or enhanced through computer-aided geometry determination or similar techniques, as discussed herein. Alternatively, automated detection algorithms may be applied to aid in identifying and/or manipulating the features or regions of interest.

As illustrated, the system 10 may also include a display 42 coupled to the operator workstation 40. The display 42 may be utilized to observe the reconstructed images, for instance. Additionally, the system 10 may include a printer 44 coupled to the operator workstation 40 and configured to print a copy of the one or more reconstructed images. The display 42 and the printer 44 may also be connected to the computer 36 directly or via the operator workstation 40. Further, the operator workstation 40 may include or be coupled to a picture archiving and communications system (PACS) 46. It should be noted that PACS 46 might be coupled to a remote system 48, radiology department information system (RIS), hospital information system (HIS) or to an internal or external network, so that others at different locations can gain access to the image data.

Although only one operator workstation is depicted, one or more operator workstations 40 may be linked in the system 10 for outputting system parameters, requesting examinations, viewing images, and so forth. In general, displays 42, printers 44, workstations 40, and similar devices supplied within the system 10 may be local to the data acquisition components, or may be remote from these components, such as elsewhere within an institution or hospital, or in an entirely different location, linked to the image acquisition system 10 via one or more configurable networks, such as the Internet, virtual private networks, and so forth.

Although the previous discussion discloses typical embodiments of the imaging system 10, it will be appreciated by those skilled in the art, that similar configurations may be employed to acquire CT images. For example, in one embodiment, the imaging system 10 may include a LightSpeed Volume CT (VCT) manufactured by General Electric Company having headquarters in Fairfield, Conn. The VCT is a 64-detector scanner that captures 64 slices of a patient's anatomy, where each slice is less than 0.36 mm wide, for a total of about 40 mm width of a patients anatomy. Other embodiments may include other number of slices and slice widths. For example, in one embodiment a 16-slice CT scanner including a spiral acquisition path can be used to capture data over a greater axial FOV.

Figure 2:
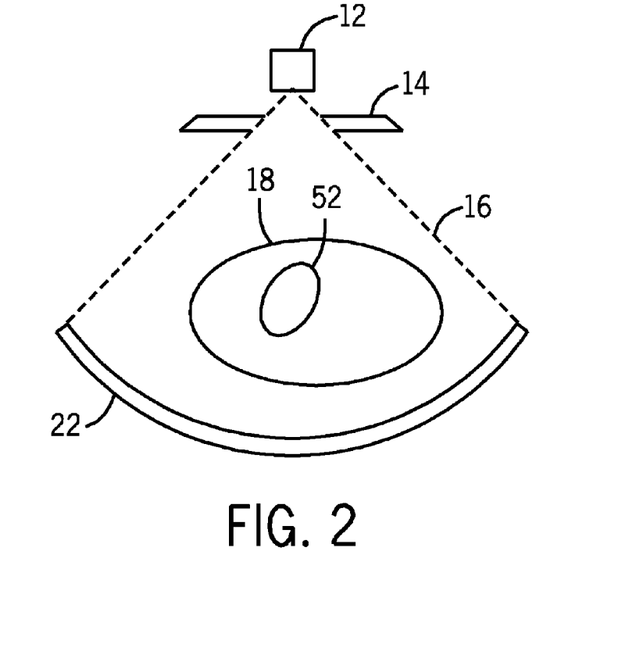
FIG. 2 is a diagrammatical illustration of a full FOV scan of a patient torso, in accordance with one aspect of the present technique.
Figure 3:
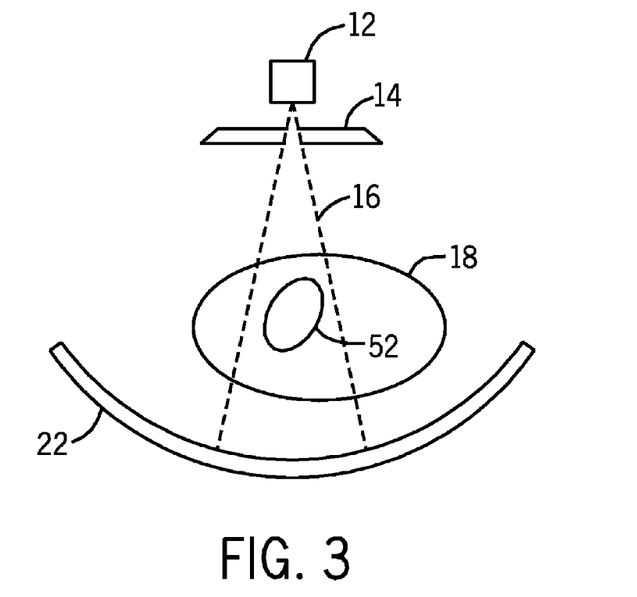
FIG. 3 is a diagrammatical illustration of a target FOV scan of a patient heart region, in accordance with one aspect of the present technique.

FIGS. 2 and 3 illustrate an exemplary medical application of one aspect of the present technique, namely CT cardiac imaging. FIG. 2 shows the essential CT scan geometry for a full scan FOV of a patient's torso including the region of the heart. An X-ray source 12 emits a fan beam of X-rays 16 in which the width of the beam is determined by the position and aperture of the collimator 14. The X-ray fan beam 16 is wider than the patient's torso 18 for the full scan FOV image acquisition. After passing through the attenuating tissues of the patient 18, the remaining X-rays 16 impact the detector 22 that measures the X-ray flux or counts X-ray photons. FIG. 3 is similar to FIG. 2 except that the collimator 14 has a narrower aperture that restricts the X-ray fan beam width to encompass the targeted FOV 52 (e.g., heart region). The full scan FOV 18 (e.g., torso) is not fully illuminated by the X-ray beam 16. Those skilled in the art will recognize that the X-ray dose to the patient may be significantly less during a target FOV scan as compared to a full FOV scan.

In this exemplary illustration, the patient's heart (targeted FOV 52) is positioned near the axis of rotation of the CT scanner. That is, the distance from the source 12 to the heart 52 is approximately constant while the source rotates rapidly around the patient 18 during the CT scan. Similarly, the detector 22 also remains approximately equidistant from the heart 52 during the CT scanner rotation. Those skilled in the art will recognize that this central position of the targeted FOV simplifies the required motion of the collimator in adjusting between the full FOV scan and the targeted FOV scan. The required width of the fan beam 16 and the patient dose are minimized by positioning the targeted FOV near the CT scanner axis of rotation.

As previously mentioned, an image of a local region (e.g., targeted FOV) that is less than a full FOV (e.g., full scan FOV) for the imaging system 10 may be employed in accordance with certain imaging techniques. For example, in cardiac imaging, a high-resolution image of a small sub-region (e.g., a targeted FOV) of a patient's anatomy, such as the heart, may be desired. Those of ordinary skill in the art will appreciate that image reconstruction for this targeted FOV using iterative reconstruction techniques may be complicated by a variety of factors. For example, data outside of the targeted FOV may or may not enhance the reconstruction of the portion of the image associated with the targeted FOV. One technique for targeted iterative reconstruction involves ignoring the signal from outside the targeted FOV, which may be referred to as "naïve reconstruction." Such a technique may result in an anomalous image where the entire signal from outside the targeted FOV is assigned to the periphery of the targeted FOV or the signal from outside the targeted FOV may produce aliasing artifacts within the targeted FOV. In other cases, an image of the full scan FOV may be reconstructed at high resolution from which the image for the targeted FOV may be extracted. Such a technique may be referred to as "brute-force reconstruction." These techniques for targeted iterative reconstruction, however, may inaccurately handle the signal from outside the targeted FOV and/or may handle the signal in a computationally expensive manner.

Figure 4:
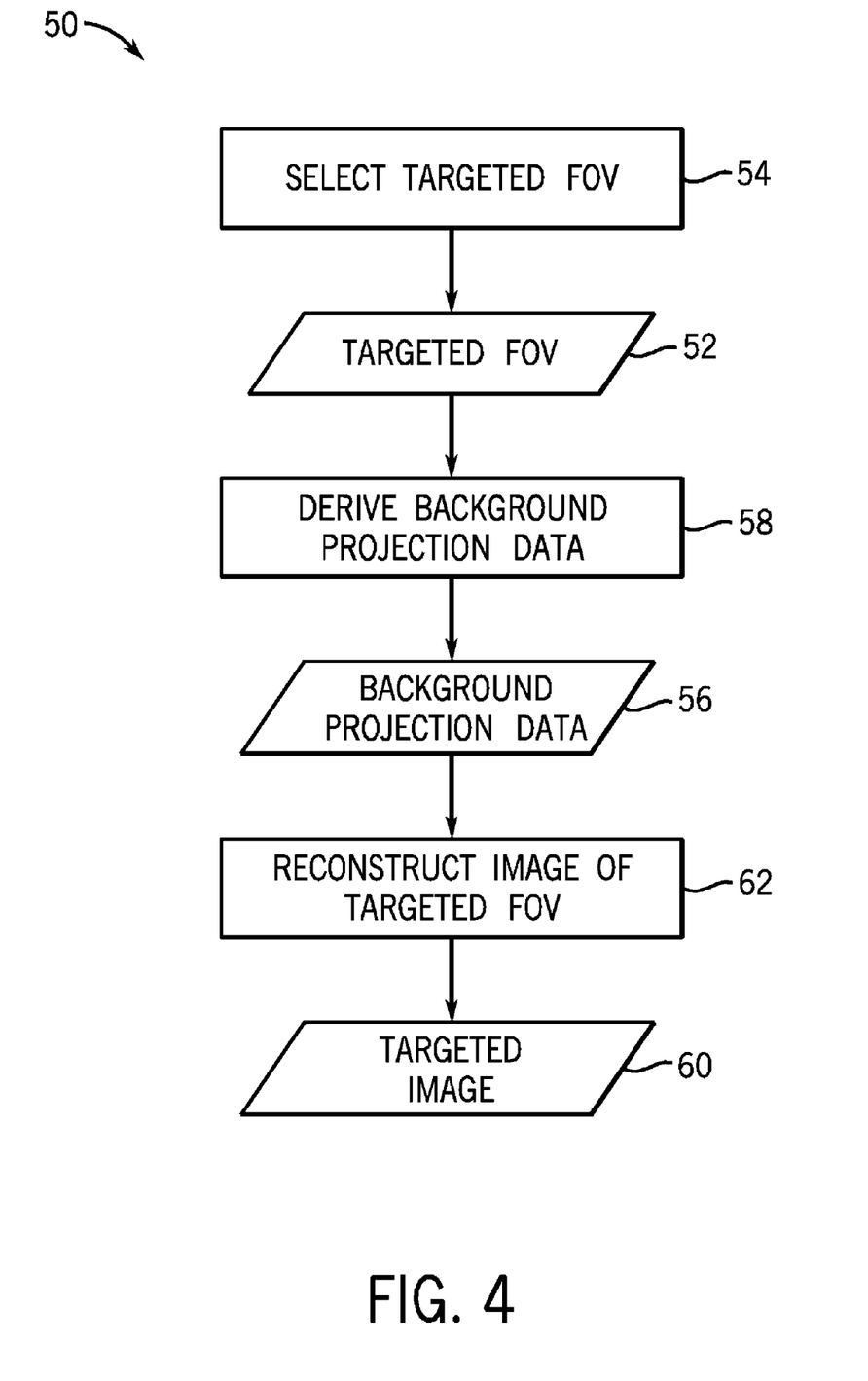
FIG. 4 is a flowchart depicting one technique for image reconstruction, in accordance with one aspect of the present technique.

To address these and associated issues with iterative reconstruction of an image of a targeted FOV, one or more embodiments of the present technique provide a method for image reconstruction. Referring now to FIG. 4, a flow chart depicting a method 50 associated with aspects of the present technique is presented. In the present technique, a targeted FOV 52 for a tomographic image may be selected, as depicted by block 54 of FIG. 4. As those of ordinary skill in the art will appreciate, the targeted FOV 52 of the tomographic image is less than or equal to the full scan FOV of the imaging system 10. For example, the full scan FOV may include the entire patient, or a significant portion of a patient, such as the patient's torso, whereas the targeted FOV may include a region that is less than the full scan FOV, such as the region including and surrounding the patient's heart. In general, the targeted FOV 52 may be selected by any suitable technique, including by a user, automatically, or semi-automatically. Next, background projection data 56 for the area outside the targeted FOV 52 of the tomographic image may be derived, as depicted at block 58. Derivation of an exemplary background projection data 56 is described in more detail below with respect to FIG. 5. In transmission imaging (e.g., X-ray CT), the background projection data 56 generally may represent attenuation of photon flux from the area outside the targeted FOV 52. Any suitable technique may be used to determine this background projection data 56. The background projection data 56 may then be used as an additional factor in the reconstruction of the targeted tomographic image 60 of the targeted FOV 52, as depicted at block 62. Reconstructing the targeted image 60 using the background projection data 56 may provide reduced artifacts and/or reduced reconstruction time as compared to alternative reconstruction techniques. Exemplary techniques for determining the background projection data 56 and for reconstructing the targeted image 60 will be discussed in the sections that follow.

Figure 5:
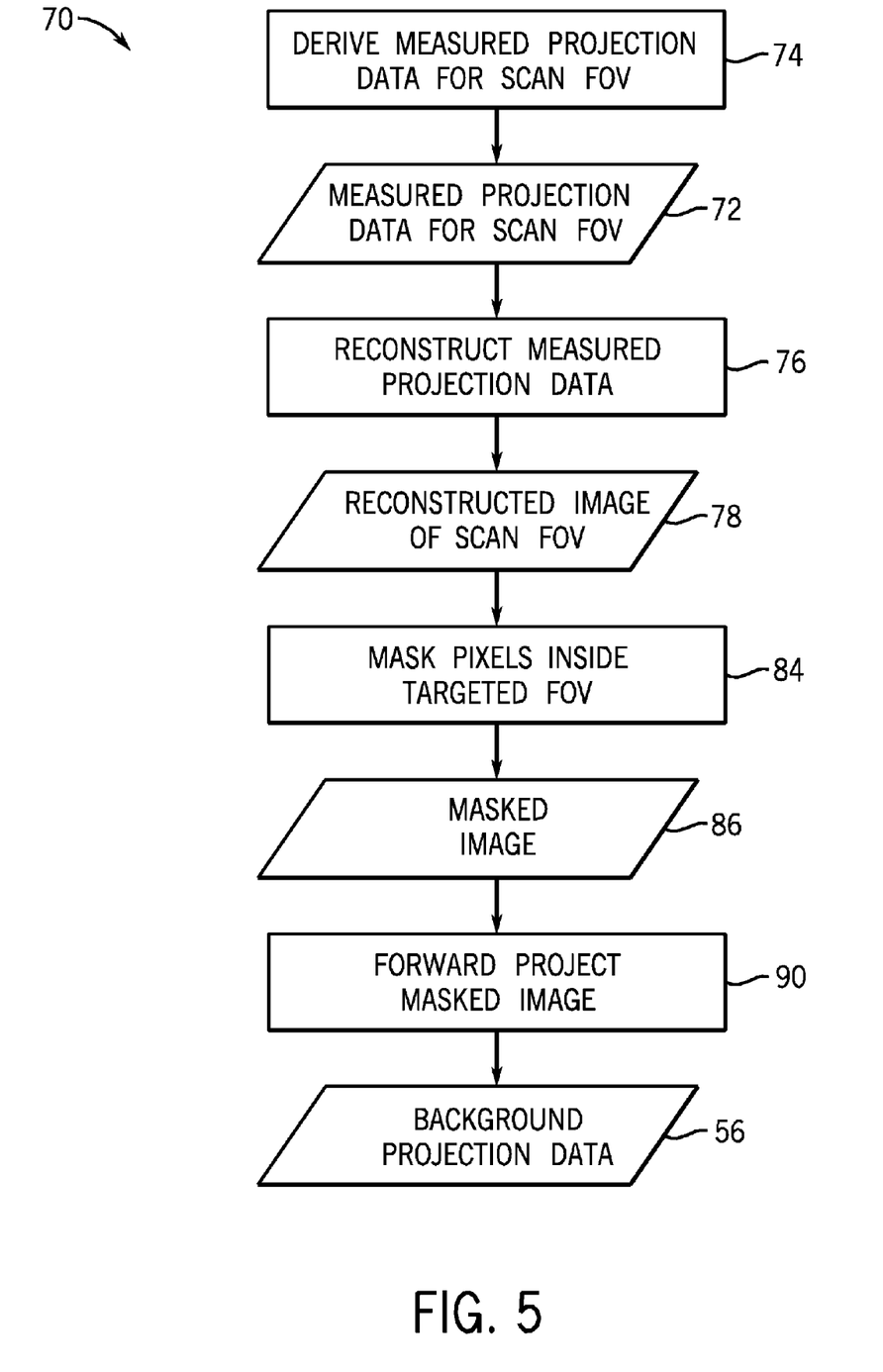
FIG. 5 is a flowchart depicting one technique for determining background projection data for an area outside a targeted FOV, in accordance with one aspect of the present technique.
Figure 6:
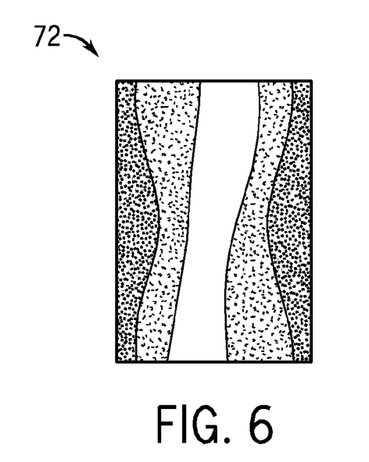
FIG. 6 is a diagrammatical view of measured projection data for a scan FOV, in accordance with one aspect of the present technique.
Figure 7:
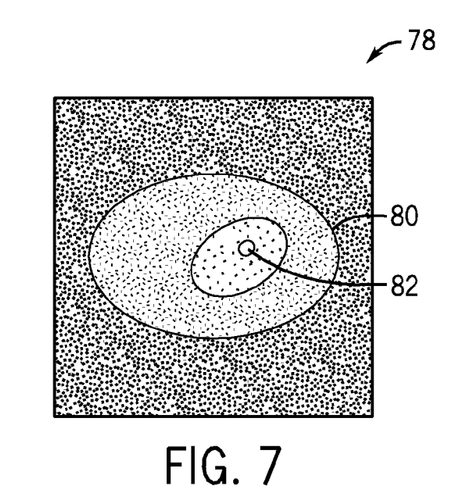
FIG. 7 is a diagrammatical view of a reconstructed image of the measured projection data of FIG. 6, in accordance with one aspect of the present technique.

Referring now to FIG. 5, a flowchart depicting an exemplary method 70 is presented for deriving the background projection data 58 of FIG. 4. Measured projection data 72 for a scan FOV of the tomographic image may be derived, as depicted at block 74. In general, the measured projection data 72 may contain data indicative of a full scan FOV. Exemplary measured projection data 72 for a scan FOV is represented as a sinogram in FIG. 6, where the vertical axis represents projection angle and the horizontal axis represents detector offset. Returning to FIG. 5, this measured projection data 72 may be reconstructed, as depicted at block 76, to obtain a reconstructed image 78 of the scan FOV. An exemplary reconstructed image 78 of the scan FOV is depicted in FIG. 7. In the reconstructed image 78 of FIG. 7, the subject imaged is represented by elliptical region 80, and the feature of interest is represented by elliptical region 82. As those of ordinary skill in the art will appreciate, any suitable reconstruction technique may be utilized to obtain the reconstructed image 78 of the scan FOV, including analytical reconstruction and iterative reconstruction algorithms. For example, full convergence of an iterative reconstruction algorithm may not be necessary for the image reconstruction of the scan FOV because only a reasonable estimate of the background projection data 56 may be needed. In other words, an image generated with less number of iterations through an iterative reconstruction algorithm may be needed to obtain the background projection data 56 than would be required to accurately reconstruct a reliable image of the scan FOV. In another example, the pixel grid utilized for this reconstruction of the scan FOV may have lower resolution than the pixel grid used for reconstruction of the targeted FOV.

Figure 8:
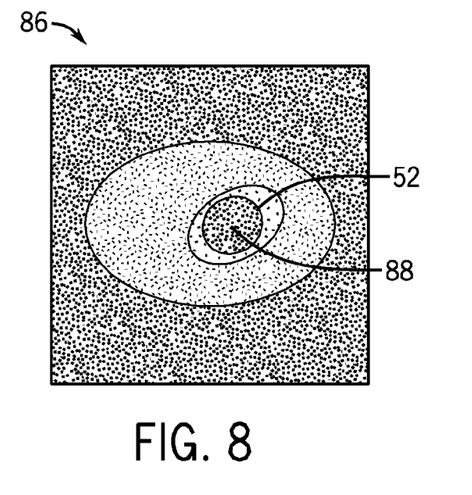
FIG. 8 is a diagrammatical view of the reconstructed image of FIG. 7 with the pixels corresponding to the targeted FOV masked out, in accordance with one aspect of the present technique.
Figure 9:
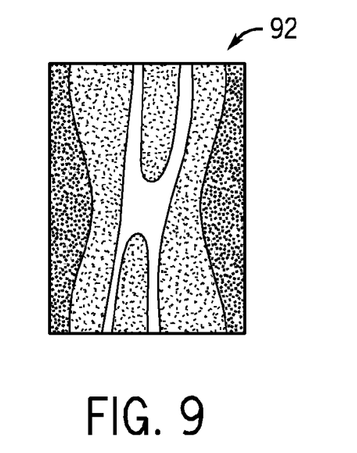
FIG. 9 is a diagrammatical view of a forward projection of the reconstructed image of FIG. 8, in accordance with one aspect of the present technique.

Once the reconstructed image 78 for the scan FOV has been obtained at block 76, pixels inside the targeted FOV may be masked out in the reconstructed image 78, as depicted at block 84. By way of example, masking out the pixels may include zeroing the pixels in the reconstructed image 78 that are inside the targeted FOV 52. An exemplary masked image 86 is depicted by FIG. 8. In the masked image 86, the targeted FOV is represented by numeral 52, and the masked pixels (all pixels inside the targeted FOV 52) are represented by number 88. To obtain the background projection data 56 for the area outside the targeted FOV 52, the masked image 86 may be forward projected, as depicted at block 90. As previously mentioned, the background projection data 56 generally may represent the activity outside the targeted FOV 52. Referring now to FIG. 9, exemplary background projection data 56 is depicted in a background sinogram 92.

Figure 10:
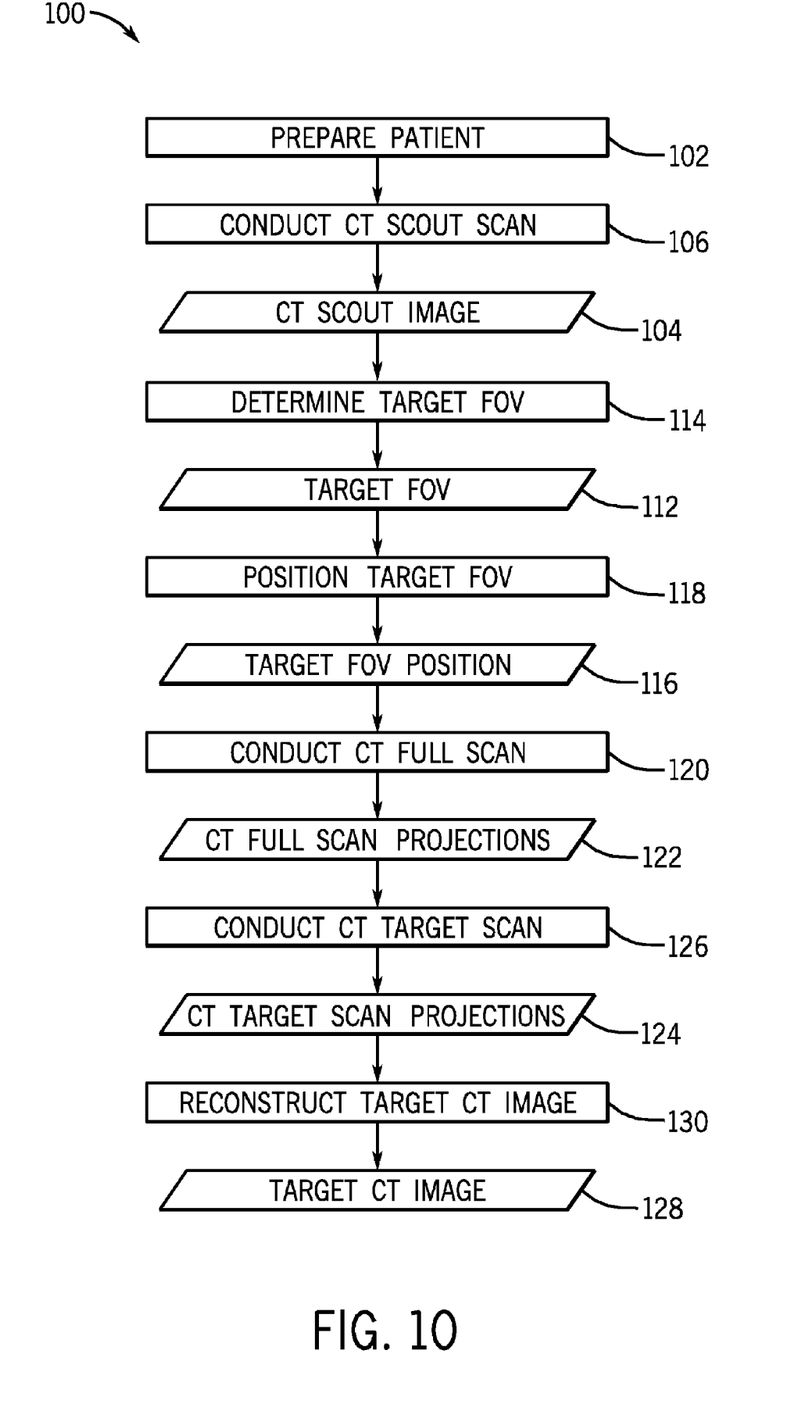
FIG. 10 is a flowchart depicting one technique for utilizing background projection data in an iterative reconstruction algorithm, in accordance with one aspect of the present technique.

Referring now to FIG. 10, a flow chart depicting a method 100 associated with aspects of the present technique is presented. More specifically FIG. 10 depicts one embodiment of acquiring and reconstructing a cardiac CT image, in accordance with the present technique. In the present technique, a patient is prepared prior to conducting a CT scan, as depicted at block 102. Preparing the patient may include, for example, positioning the patient's arms above the patient's head to allow for a reduction in X-radiation dose applied to the patient and to reduce bone artifacts in the image since the arms will not be included in the FOV when the CT scan is performed over certain regions of the patient, such as the patient's torso and heart. A CT scout image 104 is acquired by moving the patient rapidly through the CT system 10 while conducting a scout scan, as depicted at block 106. In one embodiment, the scout scan may include a rapid scan of all or a majority of the patient to provide data for reconstructing an image to identify locations of certain regions of interest, such as the patient's heart.

Further, the method generally includes determining a target field of view 112, as depicted at block 114. For example, a region surrounding the target (e.g., the heart) may be placed around the initial target position 108. Such a target field of view 112 may be identified from the CT scout image 104, in one embodiment. For example, where the CT scout image 104 includes the patient's heart, a target field of view 112 that identifies a sub-region that includes the patient's heart may be selected. The selected target FOV 112 may be used in positioning and imaging routines discussed below. Further, in certain embodiments, the target FOV 112 may include regions adjacent to the region of interest, such as those regions surrounding the heart that may enhance the reconstruction of the target FOV 112. For example, the target FOV 112 may include an additional region around the heart to ensure that the entire heart is imaged and/or to aid in reconstructing an image corresponding to the target FOV 112, as discussed below. Generally, determining the target FOV 112 is automated (e.g., includes image processing to determine the location of the target), however, determination of the target FOV 112 may be subject to operator verification and editing, or may be performed manually.

The target FOV 112 is then preferentially moved to a target FOV position 116, as illustrated at block 118. For example, in a preferred embodiment the table supporting the patient may be moved to center the target FOV 112 (e.g., the heart region) on the axis of rotation of the CT system 10 (e.g., the axis of rotation of the source 12 and the detector 22). With the target FOV 112 positioned relative to the system 10, a full scan is conducted and full scan projections 122 are acquired, as depicted at block 120. The full scan generally includes scanning the target FOV 112 along with regions surrounding the target FOV 112. For example, where the heart is the desired target of the CT image, and defines, at least partially, the target FOV 112, the full scan may include a scan of the patient's torso. Accordingly, the full scan projections 122 may include projections of X-rays that have passed through the patient's torso. During the full scan, the X-ray beams 16 may include a fan angle that engulfs the target FOV 112 and all or at least a significant portion of the patient's cross-section.

Further, a target scan is conducted to acquire target projections 124, as depicted at block 126. In one embodiment, the target scan generally includes reducing the fan angle of the X-ray beams 16 such that they pass primarily through the target FOV 112. In some embodiments, the fan angle may be adjusted such that the X-ray beams 16 pass through the target FOV 112 and regions proximate to the target FOV 112, but do not pass through the entire region scanned in the full scan discussed previously with regard to block 120. In one embodiment, a mechanical filter (e.g., the collimator 14) is placed between the source 12 and the patient 18 such that the mechanical filter blocks all of the X-ray beams 16, except for the portion of the X-ray beams 16 that are transmitted through the target FOV 112, thereby reducing the X-radiation dose to the patient (e.g., reducing radiation to the patient's torso). In some embodiments, the mechanical filter, or collimator 14, is formed from tungsten or other suitable X-ray absorbing material. In some embodiments, the mechanical filter may include a dynamic configuration that enables dynamic adjustment to change and/or tune the configuration (e.g., the shape and width) of the X-ray beams 16. Further, the mechanical filter may be placed close to the X-ray source 12 to facilitate a small size that is still capable of effectively reducing the width and or shape of the X-ray beams 16. Further, embodiments may include the implementation of a dynamic bowtie filter, a virtual bowtie filter, or the like to configure the X-ray beams 16.

Generally, the CT target scan, as depicted at block 126, continues for a given period of time. In one embodiment, such as that including a scan of the patient's heart, the target scan continues for a portion or all of one heart beat. In other embodiments, the target scan continues for more than one heart beat (e.g., for several heart beats). Acquiring the target scan over one or more heat beats may enable reconstruction of images that correspond to the heart (or similar dynamic organ) in various states during its operation. For example, the period of time may enable acquisition of images that are representative of the heart or a similar organ in the contracted (systole) and relaxed (diastole) states, or states in between.

The CT target scan projections 124 include the X-ray data acquired during the CT target scan 126. Accordingly, a target CT image 128 can be generated via reconstruction of the target image, as depicted at 130. For example, as discussed in greater detail below, certain embodiments of reconstructing the target image, as depicted at block 130, may include using the full scan to acquire a generally static background sinogram, masking out a region of the background sinogram where the target FOV 112 is located, and iteratively reconstructing the target CT image 128 by extracting data (e.g., keyhole data) of the target scan projection 124 and combining the keyhole data with the unmasked data of the background sinogram of the full scan projections 122. In other words, data from a single full scan can be combined with each set of data from the target scans to accurately reconstruct each of the target images associated with each of the target scans. Thus, the X-ray dose to the patient can be reduced while still generating accurate target CT images. Only a single full scan 120 is conducted to provide background data corresponding to generally static portions of a patient (e.g., the areas surrounding the heart that do not move significantly during a breath hold). During the target scan 126 the X-ray beam 16 is restricted by the collimator 14 to the region proximate to the target FOV (e.g., the heart region), thereby avoiding additional X-ray dose to the full FOV (e.g., full torso).

As previously mentioned in the discussion of FIG. 4, the background projection data 56 may be used as an additional factor in the reconstruction of a targeted image 60. As those of ordinary skill in the art will appreciate, any suitable reconstruction technique may be used to reconstruct the targeted image 60, including a variety of iterative reconstruction algorithms. One suitable technique includes utilizing the background projection data 56 as an additive correction term for a projection data estimate from the forward projected image estimate.

CT imaging depends on the transmission of at least some X-rays through the attenuating object. The standard imaging equation for X-ray CT is given by equation (1) as follows:

$$\hat{y}_i = b_i \cdot \exp\left(-\sum_j P_{i,j}\mu_j\right) + S_i \qquad (1)$$

wherein:
$\hat{y}_i$ refers to the mean photon flux detected at the detector i in the presence of the object;
$b_i$ refers to the photon flux that would have been detected at the detector i in the absence of the object;
$\mu_j$ refers to the linear attenuation coefficient of the object for the pixel j;
$S_i$ refers to the scatter flux detected at the detector i; and
$P_{i,j}$ refers to the effective intersection length of the line of response (LOR) i with pixel j.

Although X-ray imaging is often performed in the presence of an anti-scatter grid, resulting in $S_i$ approximately 0, in the absence of an anti-scatter grid, $S_i$ can be large enough not to be ignored and can be estimated by other algorithmic means. Accordingly, the data can be pre-corrected for scatter or scatter correction can be incorporated into the reconstruction loop.

CT reconstruction may be implemented using any of a variety of suitable reconstruction algorithms. As will be appreciated by those of ordinary skill in the art, CT reconstruction may utilize a Maximum Likelihood Transmission (MLTR) algorithm. An exemplary MLTR algorithm for the corrections in the loop technique that does not implement the present technique is given by equation (2):

$$\mu_j^{k,m+1} = \mu_j^{k,m} + \frac{\sum_{i \in S_m} P_{i,j} \cdot \frac{(\hat{y}_i - S_i)}{\hat{y}_i} \cdot (\hat{y}_i - y_i)}{\sum_{i \in S_m} P_{i,j} \cdot \left[\sum_{j'} P_{i,j'}\right] \cdot (\hat{y}_i - S_i) \cdot \left(1 - \frac{y_i S_i}{\hat{y}_i^2}\right)} \qquad (2)$$

Wherein:
$\mu$ refers to an image estimate, and $\mu_j^{k,m}$ refers to the image estimate for pixel j at the $k^{th}$ iteration and the $m^{th}$ subset of LORs;
$P_{i,j}$ refers to the effective intersection length of the LOR i with pixel j;
$S_i$ refers to the scatter flux detected at the detector i;
$\hat{y}_i$ refers to the mean photon flux detected at the detector i in the presence of the object;
$y_i$ refers to the measured projection data detected by the $i^{th}$ LOR; and
$S_m$ refers to the $m^{th}$ subset of LORs.

As will be appreciated, for CT reconstruction, the background projection data generally may represent attenuation of photon flux from the area outside the targeted FOV 52. Once the background projection data 56 is derived, the background projection data 56 may be used as an additional factor in the reconstruction of the targeted FOV (block 60, FIG. 4), such as in a reconstruction utilizing the above-listed MLTR algorithm. Accordingly, equation (2) can be modified to implement the reconstruction technique described herein. An exemplary iterative update equation for the corrections in the loop technique utilizing the background projection data in a MLTR algorithm is given by equation (3). It should be appreciated, however, that the present technique is applicable for implementation using any suitable iterative reconstruction update equation.

$$\mu_j^{k,m+1} = \mu_j^{k,m} + \frac{\sum_{i \in S_m} P_{i,j} \cdot \frac{(\hat{y}_i - S_i - t_i^{bkg})}{\hat{y}_i} \cdot (\hat{y}_i - y_i)}{\sum_{i \in S_m} P_{i,j} \cdot \left[\sum_{j'} P_{i,j'}\right] \cdot (\hat{y}_i - S_i - t_i^{bkg}) \cdot \left(1 - \frac{y_i(S_i + t_i^{bkg})}{\hat{y}_i^2}\right)} \qquad (3)$$

wherein:
$\mu$ refers to an image estimate, and $\mu_j^{k,m}$ refers to the image estimate for pixel j at the $k^{th}$ iteration and the $m^{th}$ subset of LORs;
$P_{i,j}$ refers to the effective intersection length of the LOR i with pixel j;
$S_i$ refers to the scatter flux detected at the detector i;
$t_i^{bkj}$ refers to the projection data resulting from attenuation of photon flux from the area outside the targeted FOV (or the background projection data);
$\hat{y}_i$ refers to the mean photon flux detected at the detector $i^{th}$ in the presence of the object;
$y_i$ refers to the measured projection data detected by the $i^{th}$ LOR; and
$S_m$ refers to the $m^{th}$ subset of LORs.

Figure 11:
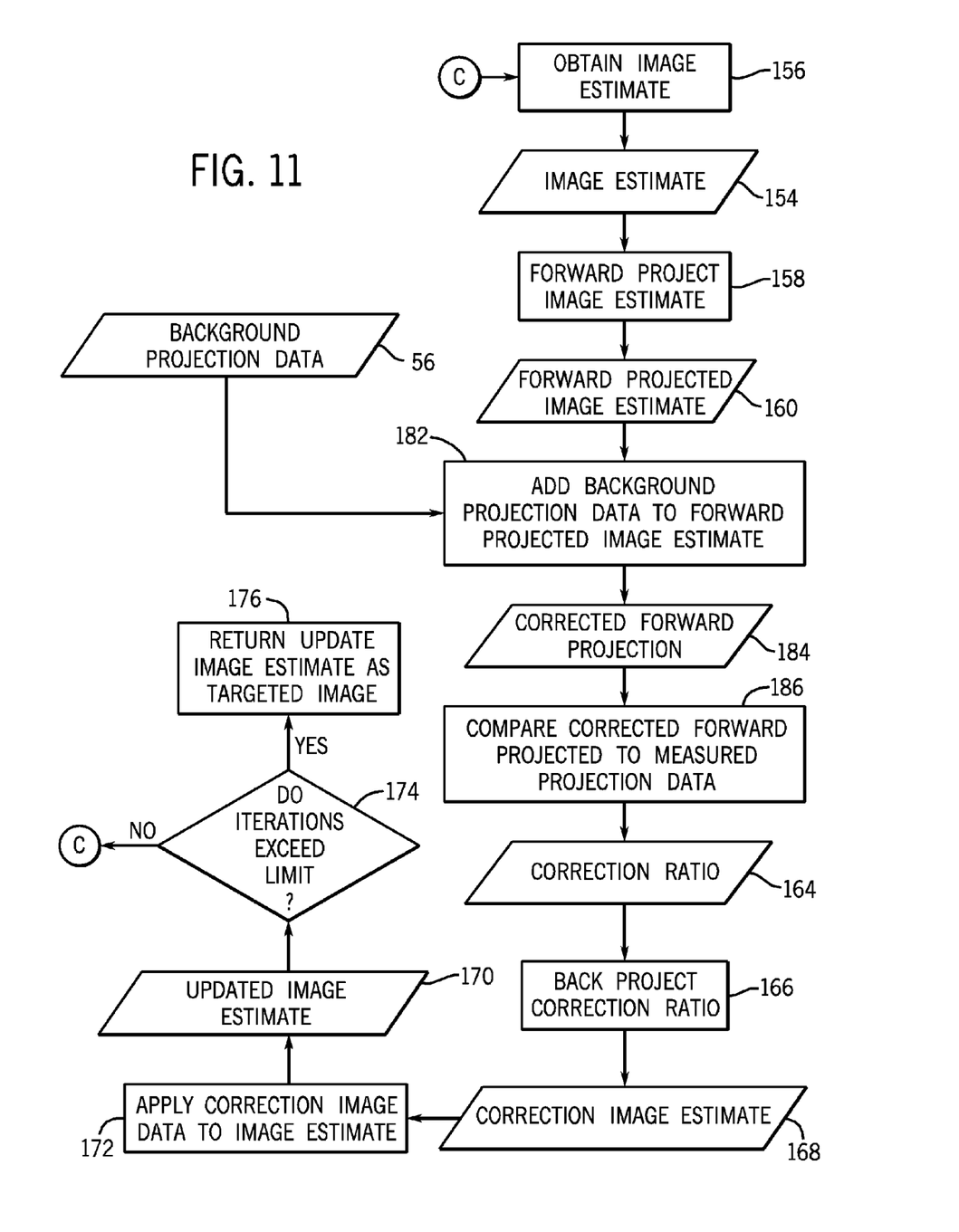
FIG. 11 is a flowchart depicting a technique for utilizing background projection data in an iterative reconstruction algorithm, in accordance with one aspect of the present technique.

Referring now to FIG. 11, a flowchart depicting this corrections-in-the-loop technique is illustrated. In the illustrated embodiment, an image estimate 154 for the targeted FOV may be obtained, as depicted at block 156. As will be appreciated, the initial image estimate 154 may take any of a number of forms and may include a uniform image or an estimate obtained from a reconstruction technique, such as filtered back projection. This image estimate 154 may then be forward projected, as depicted in block 158, to the projection plane to obtain a forward projected image estimate 160.

An exemplary technique for determining the background projection data 56 was discussed above with respect to FIG. 5. This background projection data 56 may be then added to the forward projected image estimate 160 as an additive corrective term, as depicted at block 182 to obtain a corrected forward projection 184. As will be appreciated, the forward projected image estimate 160 may also be corrected for photon scatter, dead time, detector efficiency, scanner geometric effects, and so forth.

This corrected forward projection 184 then may be compared to the measured target scan projection data 124, as depicted at block 186. For example, this comparison may include taking the ratio of the measured projection data 124 and the corrected forward projection 184 to obtain a correction ratio 164. As depicted at block 166, the correction ratio 164 may be back projected to obtain correction image data 168. An updated estimated image 170 may then be obtained by applying the correction image data 168 to the image estimate 154, as depicted at block 172. In one embodiment, the corrected image data 168 and the image estimate 154 are multiplied to obtain the updated image estimate 170 for the targeted FOV. As will be appreciated, the updated image estimate 170 becomes the image estimate 154 to be used in the next iteration. As depicted at block 174, it is determined whether the number of iterations for generating the image for the targeted FOV exceeds a threshold value. If the number of iterations exceeds the threshold value, the updated image estimate 170 is returned, as depicted at block 176, as the targeted image 60. Alternatively, rather than using a threshold value, it may be determined whether convergence between the image estimate 154 and the updated image estimate 170 has reached a desired level. Otherwise, the technique of FIG. 11 starting at block 156 is performed iteratively.

As will be appreciated by those of ordinary skill in the art, the embodiment illustrated by FIG. 11 may be implemented utilizing the Maximum Likelihood Transmission (MLTR) algorithm. While the MLTR algorithm may be employed as discussed above, other embodiments of the present technique may be implemented using any suitable iterative reconstruction update equation.

As will be appreciated by those of ordinary skill in the art the exemplary techniques described herein are applicable to both static reconstruction, as well as motion compensated reconstruction, such as motion compensated CT reconstruction. As mentioned above, the background projection data 56 may also be used as an additional factor in a motion compensated reconstruction. In motion compensated reconstruction, the reconstruction is applied to four dimensions wherein the fourth dimension is time gating. By way of example, multiple gates of data are acquired based on time dependent gating, for example, on respiratory gating or cardiac gating. However, while the multiple gates of data are time dependent, the background projection data 56 derived for use in the motion compensated reconstruction need not be time dependent. For example, a low resolution, motion uncompensated image may be used to derive the background projection data 56. The motion uncompensated image may be reconstructed from a sum of all the projection gates of data or from single breath-hold CT full scan projections 122. From this motion uncompensated image, the background projection data 56 may be derived, for example, by masking out the pixels within the targeted FOV 52 and then forward projecting the masked image 86, in accordance with the exemplary embodiment of FIG. 5. To obtain the background projection data for each of the projection gates, the background projection data 56 may be scaled by the relative acquisition times of each corresponding projection gate. Exemplary embodiments of the present technique may be implemented using any suitable motion compensated reconstruction update equation.

As previously discussed, the exemplary techniques of the present technique provide a method for the iterative reconstruction of an image of a targeted FOV that is less than the full scan FOV. As described above, reconstruction of a targeted image (such as targeted image 60) in accordance with embodiments of the present technique may provide reduced artifacts as compared to alternative reconstruction techniques. Artifacts, however, may appear in the targeted image 60 due to a variety of factors.

Figure 12:
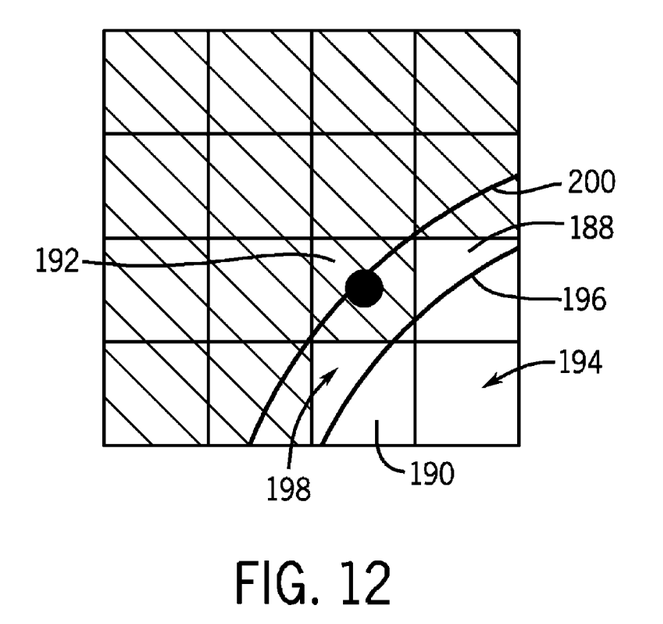
FIG. 12 is an expanded diagrammatical view of a targeted FOV, in accordance with one aspect of the present technique.

In one instance, pixels that straddle the targeted FOV may result in artifacts on the edges of the targeted image 60. By way of example, these artifacts may occur when the background projection data 56 representing activity outside the targeted FOV is subtracted from the measured projection data 72, in accordance with aspects of the present technique. As illustrated by FIG. 12, pixels 188, 190, 192 are shown straddling the targeted FOV 194. The edge of the targeted FOV is represented on FIG. 12 by numeral 196. In the illustrated embodiment, the targeted FOV 194 is defined to include all pixels having a center within the targeted FOV 194. Accordingly, pixels 188 and 190 are shown within the targeted FOV 194. Pixel 192, however, does not have a center within the targeted FOV 194 and, thus, is not shown as within the targeted FOV 194. Because pixel 192 extends into the targeted FOV 194 while not being defined as within the targeted FOV 194, artifacts may occur in the reconstructed image. For instance, pixel 192 will not be masked out during determination of the background projection data 56, in accordance with certain aspects of the present technique.

To address this issue, the targeted FOV 194 may be expanded so that any pixel extending partially into the targeted FOV 194, such as pixel 192, may be considered within the expanded targeted FOV 198. For example, the targeted FOV 194 may be expanded beyond the targeted FOV that was originally identified. By way of example, the expanded targeted FOV may be defined as the targeted FOV 194 plus a buffer zone 198. The edge of the buffer zone 198 is represented on FIG. 12 by numeral 200. In one embodiment, this buffer zone 198 may expand beyond the original targeted FOV by a distance equal to sqrt(½) of a pixel width. As illustrated on FIG. 12, the targeted FOV 194 may be expanded so that pixel 192 that previously straddled the targeted FOV is inside the buffer zone 198.

Figure 13:
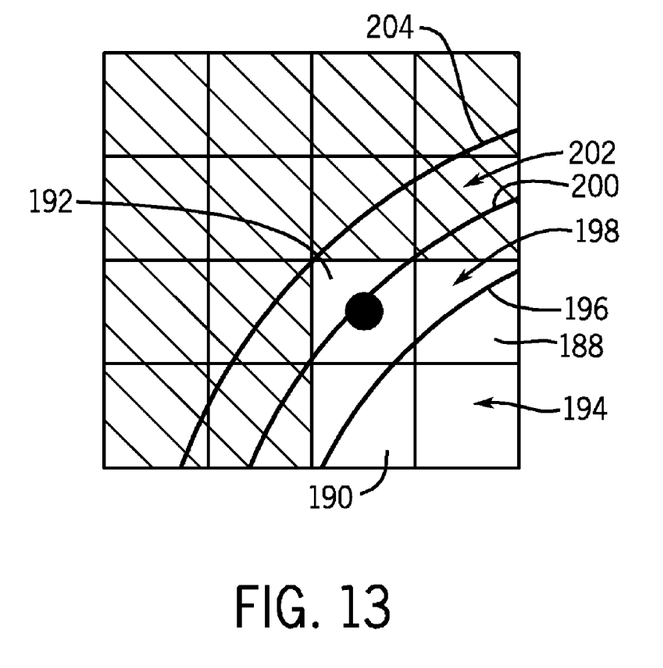
FIG. 13 is an expanded diagrammatical view of a targeted FOV, in accordance with one aspect of the present technique.

In another embodiment, the targeted FOV 194 may be expanded so that the entire pixel 92 (and not just the center) is contained within a second buffer zone 202 for the targeted FOV 194. The second buffer zone 202 may extend beyond the first buffer zone 198 by a distance of sqrt(½) of a pixel width. The edge of the second buffer zone 202 is represented on FIG. 13 by numeral 202. Including the entire pixel 192 within the expanded targeted FOV may ensure, for example, that the pixel 192 will be represented in the targeted reconstruction. As will be appreciated, the targeted image may be constructed for this expanded targeted FOV 198, in accordance with an embodiment of the present technique. The portion of the targeted image that extends beyond the original targeted FOV 194 may be trimmed so that the final reconstructed image is for the targeted FOV 194. For example, the reconstructed portion of buffer zone 198 and second buffer zone 202 may be trimmed from the targeted image.

The targeted FOV may also be expanded for motion compensated reconstruction. As those of ordinary skill in the art will appreciate, projection data from the different gates may be reconstructed independently and subsequently registered and combined. Alternatively, the motion estimates, on a voxel-by-voxel basis, can be incorporated into an iterative reconstruction algorithm that uses all the projection data. In either case, motion estimates are generally made on a voxel-by-voxel basis. However, motion (such as cardiac or respiratory motion) may cause voxels at the edge of the targeted FOV to move in and out of the targeted FOV. Accordingly, the targeted FOV may be expanded to include a buffer zone. The buffer zone may include the range of motion of all voxels inside the targeted FOV. After image reconstruction, this buffer zone may be trimmed from the reconstructed image.

In addition, artifacts in the targeted image may also be due to pixel discontinuities in the reconstructed image of the scan FOV that may forward project as streaks through an image of the targeted FOV. To address this issue, projection data filtering may be applied after a forward projection step, such as after block 158 on FIG. 11. In one exemplary embodiment, the projection data filtering may be based on the relative size of the scan FOV pixel versus the element width for the projection data.

While the present discussion does not reference image shifts and rotations applied during the course of image reconstruction, those of ordinary skill in the art will appreciate that these shifts and rotations may be applied in accordance with aspects of the present technique. For example, because the targeted reconstruction coordinates are defined with respect to the output coordinate system, which may be rotated with respect to, for example, the CT gantry, the measured projection data for the scan FOV 72 may be reconstructed (block 76) and forward projected (block 90) with the shift and rotation parameters applied. In one embodiment, the shift and rotation parameters may be ignored in the reconstruction of the measured projection data (block 76) while the definition of the targeted FOV includes the shift and rotation parameters. In another embodiment, the shift and rotation parameters may be applied to the reconstruction of the measured projection data (block 76). In both instances, the forward projection (block 90) should match the reconstruction of the measured projection data (block 76).

As noted above, while specific reference is made in the present discussion to a X-ray CT imaging system 10, it should be appreciated that the present technique is not intended to be limited to these or to any specific type of imaging system or modality. In general, the present technique may be used for image reconstruction with transmission imaging modalities that use line integral projection tomography reconstruction. Examples include limited angle tomography (X-ray tomosynthesis) and gamma-ray transmission imaging (as used in some PET and SPECT systems for attenuation map imaging). Such imaging modalities are particularly suited for reconstructing images of a targeted FOV that is less than the scan FOV for the imaging system 10.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of acquiring and reconstructing a computed tomography image, comprising:
   acquiring background computed tomography projection data;
   acquiring target region computed tomography projection data limited to a target field of view; and
   iteratively reconstructing the computed tomography image based on the background computed tomography projection data and the target region computed tomography projection data, wherein a key-hole region of the background computed tomography projection data is replaced with the projection data corresponding to the target field of view.

2. The method of claim 1, wherein the target field of view comprises a heart region.

3. The method of claim 2, wherein acquiring target region computed tomography projection data comprises acquiring the target region projection data over a portion of one heart beat cycle or over one or more heart beat cycles.

4. The method of claim 1, wherein acquiring target region computed tomography projection data limited to a target field of view comprises use of a collimator to limit the source X-rays to a target field of view.

5. The method of claim 1, wherein the background computed tomography projection data is derived from a full scan field of view.

6. The method of claim 5, wherein the full scan field of view comprises a field of view including a patient torso.

7. The method of claim 1, wherein iteratively reconstructing the computed tomography image comprises iteratively reconstructing a one- or two- or three- or four-dimensional computed tomography image.

8. The method of claim 1, wherein the background computed tomography projection data comprise data indicative of a generally static background.

9. A method of acquiring a computed tomography (CT) image comprising:
   acquiring a scout image of a patient with a CT scanner;
   determining a target field of view;
   positioning the target field of view near to an axis of rotation of the CT scanner;
   performing a full scan to acquire projection data of a full field of view;
   performing a target scan, wherein the target scan comprises restricting X-rays to the width of the target field of view; and
   replacing a key-hole region of the projection data of the full field of view with projection data corresponding to the target field of view.

10. The method of claim 9, wherein the target field of view comprises a region including a heart.

11. The method of claim 9, wherein the target field of view comprises a subset of the full scan field of view.

12. The method of claim 9, wherein positioning the target field of view near to an axis of rotation of the CT scanner comprises moving a patient on a patient support relative to the scanner.

13. The method of claim 9, wherein performing a full scan comprises scanning a torso region of a patient.

14. The method of claim 9, wherein performing a target scan comprises scanning the target field of view by restricting X-rays to the width of the target field of view by use of a collimator.

15. The method of claim 9, wherein performing a target scan comprises acquiring target scan data over an extended period of time.

16. The method of claim 15, wherein the extended period of time comprises a portion of one heart beat cycle or one or more heart beat cycles.

17. The method of claim 15, comprising reconstructing a four dimensional CT image based on full scan data associated with performing a full scan and target scan data associated with the target scan data acquired over the extended period of time.

18. A method of reconstructing a computed tomography (CT) image, comprising:
   iteratively reconstructing the CT image using full field of view (FOV) projection data and
   replacing a key-hole region of the full FOV projection data with target FOV projection data.

19. The method of claim 18, wherein the target FOV projection data comprises data obtained from a heart region over a portion of one heart beat cycle or over one or more heart beat cycles.

20. The method of claim 19, wherein the full field of view projection data comprises data obtained from a torso during a single breath hold.

21. A non-transitory computer readable medium comprising a program configured to:
   iteratively reconstruct a computed tomography (CT) image based on full field of view projection data associated with a CT full scan and target scan projection data associated with a CT target scan having a target field of view, wherein reconstructing the CT image comprises replacing a key-hole region of the full field of view projection data with projection data corresponding to the target field of view data.

* * * * *